US012749555B2

(12) United States Patent
Izadi et al.

(10) Patent No.: US 12,749,555 B2
(45) Date of Patent: Sep. 29, 2026

(54) MULTIPOLE MOMENT BASED COARSE GRAINED REPRESENTATION OF ANTIBODY ELECTROSTATICS

(71) Applicant: GENENTECH, INC., South San Francisco, CA (US)

(72) Inventors: Saeed Izadi, South San Francisco, CA (US); Thomas W. Patapoff, South San Francisco, CA (US); Benjamin T. Walters, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 1282 days.

(21) Appl. No.: 17/587,797

(22) Filed: Jan. 28, 2022

(65) Prior Publication Data

US 2022/0148676 A1 May 12, 2022

Related U.S. Application Data

(63) Continuation of application No. PCT/US2020/044259, filed on Jul. 30, 2020.

(Continued)

(51) Int. Cl.
*G16B 15/30* (2019.01)

(52) U.S. Cl.
CPC .................................... *G16B 15/30* (2019.02)

(58) Field of Classification Search
None
See application file for complete search history.

(56) References Cited

U.S. PATENT DOCUMENTS

2007/0135998 A1 6/2007 Van Vlijmen et al.
2017/0091377 A1 3/2017 Sharma et al.

FOREIGN PATENT DOCUMENTS

WO WO-2005038596 A2 * 4/2005 ............ G16C 20/50
WO 2014186692 A1 11/2014
WO WO-2017155840 A1 * 9/2017 ............ G16B 50/20

OTHER PUBLICATIONS

Agrawal, N. J., Helk, B., Kumar, S., Mody, N., Sathish, H. A., Samra, H. S., . . . & Trout, B. L. (Jan. 2016). Computational tool for the early screening of monoclonal antibodies for their viscosities. In MAbs (vol. 8, No. 1, pp. 43-48). Taylor & Francis. (Year: 2016).*

(Continued)

*Primary Examiner* — Kaitlyn L Minchella
*Assistant Examiner* — Noah A. Auger
(74) *Attorney, Agent, or Firm* — Kilpatrick Townsend & Stockton LLP

(57) ABSTRACT

The present disclosure relates to polypeptide therapeutics, and in particular to techniques for prediction of polypeptide properties that may make for suitable polypeptide therapeutics using a model representative of electrostatics of a polypeptide. Particularly, aspects of the present disclosure are directed to ascertaining molecular multipole moments of an antibody molecule, creating a model of the antibody molecule by selecting sites within a representation of the antibody molecule, calculating a charge for each of the sites, where a combination of calculated charges for the sites approximates the molecular multipole moments of the antibody molecule, and simulating interactions of molecules in a solution. At least one molecule of the molecules in the solution is an instance of the model of the antibody molecule and the interactions are simulated based on the charges calculated for each of the sites within the representation of the antibody molecule.

20 Claims, 8 Drawing Sheets

Related U.S. Application Data

(60) Provisional application No. 63/009,712, filed on Apr. 14, 2020, provisional application No. 62/882,092, filed on Aug. 2, 2019.

(56) References Cited

OTHER PUBLICATIONS

Shen, H., Li, Y., Ren, P., Zhang, D., & Li, G. (2014). Anisotropic coarse-grained model for proteins based on Gay-Berne and electric multipole potentials. Journal of chemical theory and computation, 10(2), 731-750. (Year: 2014).*

Golubkov, P. A., & Ren, P. (2006). Generalized coarse-grained model based on point multipole and Gay-Berne potentials. The Journal of chemical physics, 125(6). (Year: 2006).*

Gramada, A., & Bourne, P. E. (2011). Coarse-graining the electrostatic potential via distributed multipole expansions. Computer Physics Communications, 182(7), 1455-1462. (Year: 2011).*

Liwo, A., Baranowski, M., Czaplewski, C., Gołaś, E., He, Y., Jagieła, D., . . . & Zaborowski, B. (2014). A unified coarse-grained model of biological macromolecules based on mean-field multipole-multipole interactions. Journal of molecular modeling, 20(8), 2306. (Year: 2014).*

Li, M., Liu, F., & Zhang, J. Z. (2016). TMFF A Two-Bead Multipole Force Field for Coarse-Grained Molecular Dynamics Simulation of Protein. Journal of chemical theory and computation, 12(12), 6147-6156. (Year: 2016).*

"Molecular Operating Environment (MOE)", Chemical Computing Group, Website: https://www.chemcomp.com/, retrieved Jan. 27, 2022, 4 pages.

Anandakrishnan et al., "Point Charges Optimally Placed to Represent the Multipole Expansion of Charge Distributions", Plos One, vol. 8, No. 7, Jul. 4, 2013, 13 pages.

Buck et al., "Highly Viscous Antibody Solutions Are a Consequence of Network Formation Caused by Domain-Domain Electrostatic Complementarities: Insights fromCoarse-Grained Simulations", Molecular Pharmaceutics, vol. 12, No. 1, Jan. 5, 2015, pp. 127-139.

Chaudhri, et, al., 2012. "Coarse-Grained Modeling of the Self-Association of Therapeutic Monoclonal Antibodies". The Journal of Physical Chemistry B 116: 8045-8057 (2012). https://doi.org/10.1021/jp301140u, pMID: 22694284.

Chaudhri et al., "The Role of Amino Acid Sequence in the Self-Association of Therapeutic Monoclonal Antibodies: Insights from Coarse-Grained Modeling", The Journal of Physical Chemistry B, vol. 117, Issue 5, Feb. 2013, pp. 1269-1279.

Chowdhury et al., "Coarse-Grained Molecular Dynamics Simulations for Understanding the Impact of Short-Range Anisotropic Attractions on Structure and Viscosity of Concentrated Monoclonal Antibody Solutions", Molecular Pharmaceutics, vol. 17, No. 5, Feb. 26, 2020, pp. 1748-1756.

Darden, et al., "Particle mesh Ew ald: An N•log(N) method for Ew ald sums in large systems". Journal of Chemical Physics, 98(12), 10089-10092. Apr. 1993.

Dolinsky,et al., "PDB2PQR: an automated pipeline for the setup of Poisson-Boltzmann electrostatics calculations", Nucleic Acids Research, vol. 32, Web Server Issue W665-W667. Mar. 2004, 3 pages.

Ferreira. et. al., "Electrostatically Mediated Protein-Protein Interactions for Monoclonal Antibodies: A Combined Experimental and Coarse-Grained Molecular Modeling Approach", Journal of Pharmaceutical Sciences 108 , Nov. 2018, pp. 120-132.

Hopkins, et al., "Long-Time-Step Molecular Dynamics through Hydrogen Mass Repartitioning", Journal of Chemical Theory and Computation, Apr. 14, 2015;11(4):1864-74, PMID: 26574392.

Izadi et al., "Multiscale Coarse-Grained Approach to Investigate Self-Association of Antibodies", Biophysical Journal, vol. 118, No. 11, 2020, pp. 2741-2754.

Izadi, et al., "Accuracy limit of rigid 3-point w ater models", The Journal of Chemical Physics, 145, 074501, Aug. 2016, 145, PMCID PMC4991989, 10 pages.

Izadi, et. al., "Supporting information for: Multi scale Coarse-Grained 1-66 Approach to Investigate Self-Association of Antibodies", Biophysical Journal, vol. 118, No. 11, Jun. 2, 2020,4 pages.

Kielich et al., "Tensor Elements of the Molecular Electric Multi Pole Moments for All Point Group Symmetries", Chemical Physics Letters, vol. 12, Issue 1, Dec. 1971, pp. 20-24, ISSN 0009-2614 //www.sciencedirect.com/science/article/pii/00092614 71806073.

Le Grand, "SPFP: Speed without compromise—A mixed precision model for GPU accelerated molecular dynamics simulations", Computer Physics Communications, vol. 184, Issue 2, Feb. 2013, pp. 374-380.

Li et al., "Concentration Dependent Viscosity of Monoclonal Antibody Solutions : Explaining Experimental Behavior in Terms of Molecular Properties", Pharmaceutical Research, vol. 31, No. 11, Jun. 7, 2014, pp. 3161-3178.

Maier, et al., "ff14SB: Improving the Accuracy of Protein Side Chain and Backbone Parameters fromff99SB", Journal of Chemical Theory and Computation, Aug. 11, 2015;11(8):3696-713, PMID: 26574453.

Martínez, et al., "PACKMOL: A package for building initial configurations for molecular dynamics simulations", Journal of Computational Chemistry 30, Feb. 2009, 2157-2164.

Pastor, et al., "An analysis of the accuracy of Langevin and molecular dynamics algorithms", Molecular Physics, Dec. 1988, 1409-1419.

Roe, et al., "PTRAJ and CPPTRAJ: Software forProcessing and Analysis of Molecular Dynamics Trajectory Data" J. Chem. Theory Comput. Jun. 2013, 9, 3084-3095.

Ryckaert, et al., "Numerical Integration of the Cartesian Equations of Motion of a System with Constraints: Molecular Dynamics of n-Alkanes", Journal of Computational Physics, 23, Mar. 1977, pp. 327-341.

Sharma, et al., "In silico selection of therapeutic antibodies for development: viscosity, clearance, and chemical stability", Proceedings of the National Academy of Sciences of the United States of America. 111: 52, Dec. 2014, 18601-6. PMID 25512516 DOI: 10.1073/Pnas.1421779112.

Tomar et al., "Molecular Basis of High Viscosity in Concentrated Antibody Solutions: Strategies for High Concentration Drug Product Development", MABS, vol. 8, No. 2, Feb. 17, 2016, pp. 216-228.

Wang, et., al., "Structure and Relaxation in Solutions of Monoclonal Antibodies". The Journal of Physical Chemistry B (2018) 122:2867-2880,Feb. 2018.

Connolly, et al., Weak Interactions Govern the Viscosity of Concentrated Antibody Solutions: High-Throughput Analysis Using the Diffusion Interaction Parameter, Biophysical Journal, vol. 103, Jul. 2012, pp. 69-78.

Kanai, et al., Reversible Self-Association of a Concentrated Monoclonal Antibody Solution Mediated by Fab-Fab Interaction That Impacts Solution Viscosity, Journal of Pharmaceutical Sciences, vol. 97, 4219-4227 (2008).

Tomar, et al., In-Silico Prediction of Concentration-Dependent Viscosity Curves for Monoclonal Antibody Solutions, MABS (Pfizer Inc.), 2017, vol. 9 No. 3, 476-489.

Yadav, et al., Establishing a Link Between Amino Acid Sequences and Self-Associating and Viscoelastic Behavior of Two Closely Related Monoclonal Antibodies, Pharmaceutical Research (2011) 28:1750-1764.

* cited by examiner

MULTIPOLE MOMENT BASED COARSE GRAINED REPRESENTATION OF ANTIBODY ELECTROSTATICS

CROSS-REFERENCE TO RELATED APPLICATIONS

The present application is a Continuation of International Application No.: PCT/US2020/044259, filed Jul. 30, 2020, which claims priority and benefit from U.S. Provisional Application No. 62/882,092, filed on Aug. 2, 2019 and U.S. Provisional Application No. 63/009,712, filed on Apr. 14, 2020, the entire contents of which are incorporated herein by reference for all purposes.

FIELD

The present disclosure relates to polypeptide therapeutics, and in particular to techniques for prediction of polypeptide properties that may make for suitable polypeptide therapeutics using a model representative of electrostatics of a polypeptide.

BACKGROUND

Polypeptide therapeutics have been successful and now represent a significant fraction of new drug approvals. In part this success can be attributed to the high affinity and specificity that can be achieved for polypeptides such as monoclonal antibodies (mAbs) against important disease targets. The large scale production of polypeptide therapeutics poses a challenge for pharmaceutical companies to create an appropriate formulation in order to meet all requirements of the target product profile such as drug stability, compatibility with administration routes, and the like. At the present time most polypeptide therapeutics are administered intravenously; however, more convenient administration routes, such as oral, transdermal, pulmonary, and subcutaneous injection routes, are desirable due to the convenience for outpatient and home treatments. Among these administration routes, subcutaneous injections are the preferred choice for some polypeptide therapeutics. Injectable solutions used for subcutaneous injections are limited to a small injection volume (i.e., <1.5 ml). Therefore the solutions require higher concentrations of polypeptides (e.g., 50 mg/ml or more). The higher concentrations of the polypeptides changes properties of the solutions, such as aggregation, antibody elution behavior, clearance, gelation, and/or viscosity, which can significantly limit the 'injectability' of the solutions as well as bringing manufacturing difficulties to industries. Thus, identifying and controlling these properties of polypeptide therapeutics while maintaining stability for a long shelf life has become important for pharmaceutical companies.

SUMMARY

In some instances, techniques are provided to predict viscosity of an antibody molecule liquid solution. A course-grain (CG) model is used in simulations to calculate viscosity, instead of using an all-atom model. The CG model is developed by selecting a discrete number of sites and calculating charge values of the discrete number of sites to approximate electrical multipole moments of the all-atom model. By a using CG model of an antibody molecule calculations can be simplified, enabling quicker assessment of viscosity of the antibody molecule solution. If viscosity of the antibody molecule liquid solution is too high, then the antibody molecule is likely not a good candidate for high-dose subcutaneous delivery and can cause challenges to bioprocessing and formulation development. High viscosity can make the development process costly and time consuming.

In various embodiments, a computer-implemented method is provided. The method can begin with ascertaining two or more molecular multipole moments of an antibody molecule. For example, the two or more molecular multipole moments can be calculated based on a full-atom model of the molecule, or the two-or more molecular multipole moments can be retrieved from a database. A model of the antibody molecule is created by selecting sites within a representation of the antibody molecule. A number of sites is less than a number of atoms in the antibody molecule. The number of sites includes a first subset of sites and a second subsets of sites. A number of sites within the first subset is set to equal a number of molecular moments ascertained previously. A charge is calculated for each of the sites such that a combination of charges of the sites approximates the multiple moments. Further each site in the second subset has a charge value equal to a charge of a site in the first subset. After creating the model of the antibody molecule, interactions of several antibody molecules are simulated interacting in a solution, and viscosity (or other characteristic) of the antibody molecule is predicted based on the simulation. In some embodiments, the number of multiple moments is equal to or greater than three and equal to or less than twenty (e.g., six); the number of sites in the first subset is greater than the number of sites in the second subset; and/or the antibody molecule is Y-shaped.

In various embodiments, a computer-implemented method is provided that includes ascertaining a plurality of molecular multipole moments of an antibody molecule; and creating a model of the antibody molecule by selecting a plurality of sites within a representation of the antibody molecule. A number of the plurality of sites is less than a number of atoms in the antibody molecule, the plurality of sites comprises a first subset of the plurality of sites and a second subset of the plurality of sites, and a number of sites within the first subset of the plurality of sites is equal to a number of molecular multipole moments within the plurality of molecular multipole moments. The method further includes calculating a charge for each of the plurality of sites. A combination of calculated charges for the plurality of sites approximates the plurality of molecular multipole moments of the antibody molecule, and for each site of the second subset of the plurality of sites, a charge calculated for each site is equal to a charge calculated for a corresponding site of the first subset of the plurality of sites. The method further includes simulating interactions of a plurality of molecules in a solution. At least one molecule of the plurality of molecules is an instance of the model of the antibody molecule and the interactions are simulated based on the charges calculated for each of the plurality of sites within the representation of the antibody molecule. The method further includes predicting a property of the solution using data from the simulation; and outputting the predicted property of the solution.

In some embodiments, for each site of the second subset of the plurality of sites, a location of the site within the representation of the antibody molecule mirrors a location of the corresponding site of the first subset of the plurality of sites within the representation of the antibody molecule.

In some embodiments, locations of sites of the first subset of the plurality of sites and the plurality of molecular multipole moments are used to calculate charge values for the first subset of the plurality of sites.

In some embodiments, a number of the plurality of molecular multipole moments is equal to or greater than three and/or equal to or less than twenty.

In some embodiments, a number of the plurality of molecular multipole moments is six, and a number of the plurality of sites is equal to ten.

In some embodiments, ascertaining the plurality of molecular multipole moments of the antibody molecule is performed by modeling a charge distribution of the antibody molecule using an atomic model of the antibody molecule.

In some embodiments, ascertaining the plurality of molecular multipole moments of the antibody molecule is performed by receiving an electric field calculation of the antibody molecule.

In some embodiments, the number of the second subset of the plurality of sites is less than the number of the first subset of the plurality of sites; and the number of the second subset of the plurality of sites plus the number of the first subset of the plurality of sites is equal to the number of the plurality of sites.

In some embodiments, the antibody molecule is a Y-shaped protein having a first arm, a second arm, and a third arm; the first arm and the second arm are part of a Fab (antigen-binding fragment) region; the third arm is part of an Fc (fragment crystallizable) region; the first subset of the plurality of sites includes sites on the first arm and the third arm; and the second subset of the plurality of sites includes sites on the second arm, so that the second arm is modeled as a mirror image of the first arm.

In some embodiments, more sites of the plurality of sites are used to model the first arm than the third arm.

In some embodiments, the property is viscosity.

In some embodiments, the computer-implemented method further comprises facilitating development of a liquid solution comprising the antibody molecule as at least part of a therapeutic agent.

In some embodiments, the computer-implemented method further comprises, based on the predicted property of the solution: (i) adding the antibody molecule to a list of potential polypeptides to be used as at least part of a therapeutic agent, (ii) removing the antibody molecule from the list of potential polypeptides to be used as at least part of the therapeutic agent, (iii) ranking the antibody molecule within the list of potential polypeptides to be used as at least part of the therapeutic agent, or (iv) a combination thereof.

In various embodiments, a computer-implemented method is provided for that comprises: receiving electric-field data for an electric field of a molecule; processing the electric-field data to generate multipole-moment data of a plurality of multipole moments; processing the multipole-moment data to generate charge data for a plurality of sites of a coarse-grain model; inputting a plurality of coarse-grain models into a simulation to generate property data of the coarse-grain model, where the plurality of coarse-grain models include the coarse-grain model; and returning a prediction of property of the molecule using the property data of the coarse-grain model. A number of the plurality of molecular multipole moments may be equal to or greater than three and/or equal to or less than twenty.

In some embodiments, processing the multipole-moment data comprises calculating a charge for each of the plurality of sites, wherein the charge data is a combination of calculated charges for the plurality of sites, which approximates the plurality of multipole moments of the molecule.

In some embodiments, a number of the plurality of sites is less than a number of atoms in the molecule.

In some embodiments, the plurality of sites comprises a first subset of the plurality of sites and a second subset of the plurality of sites, and a number of sites within the first subset of the plurality of sites is equal to a number of molecular multipole moments within the plurality of molecular multipole moments.

In some embodiments, for each site of the second subset of the plurality of sites, a charge calculated for each site is equal to a charge calculated for a corresponding site of the first subset of the plurality of sites.

In some embodiments, the property is viscosity.

In some embodiments, the method further comprises outputting the predicted property of the molecule.

In some embodiments, the method further comprises facilitating development of a liquid solution comprising the molecule as at least part of a therapeutic agent.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present disclosure is described in conjunction with the appended figures.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

Antibody molecules have been found to be beneficial for various medical treatments. For example, an antibody is a protein that could be used by the immune system to neutralize pathogens (e.g., viruses or pathogenic bacteria). However, identifying and developing beneficial antibody molecules can be challenging. There exists a need for more efficient and/or cost-effective techniques for developing antibody molecules for medical treatments.

I.A. Viscosity of Antibody Concentrations

For an antibody to achieve a target effect, a solution containing the antibody is configured to have a sufficiently high dosage (e.g. for subcutaneous delivery) so that the antibodies can effectively reach a target destination within a subject (e.g., a human body). One challenge in designing a solution is to have a solution that has both a sufficiently high concentration antibody molecules and a sufficiently low viscosity. For example, a composition of a monoclonal antibody (mAb) might be highly viscous as a result of particular molecular configurations and charge distributions. Frequently, it is determined that a mAb has a prohibitively high viscosity only after the composition and/or delivery specifics for the mAb have been completed. Early detection of molecules that might be highly viscous can be advantageous to reduce development costs by avoiding development of solutions for molecules that will be too viscous and/or to provide opportunity for molecular redesign for highly viscous molecules. In silico screening also reduces the need to manufacture (e.g., develop a cell line, grow, and purify) and test in vitro many variants of similar antibodies to determine which of those variants have the best viscosity (among other properties).

Figure 1:
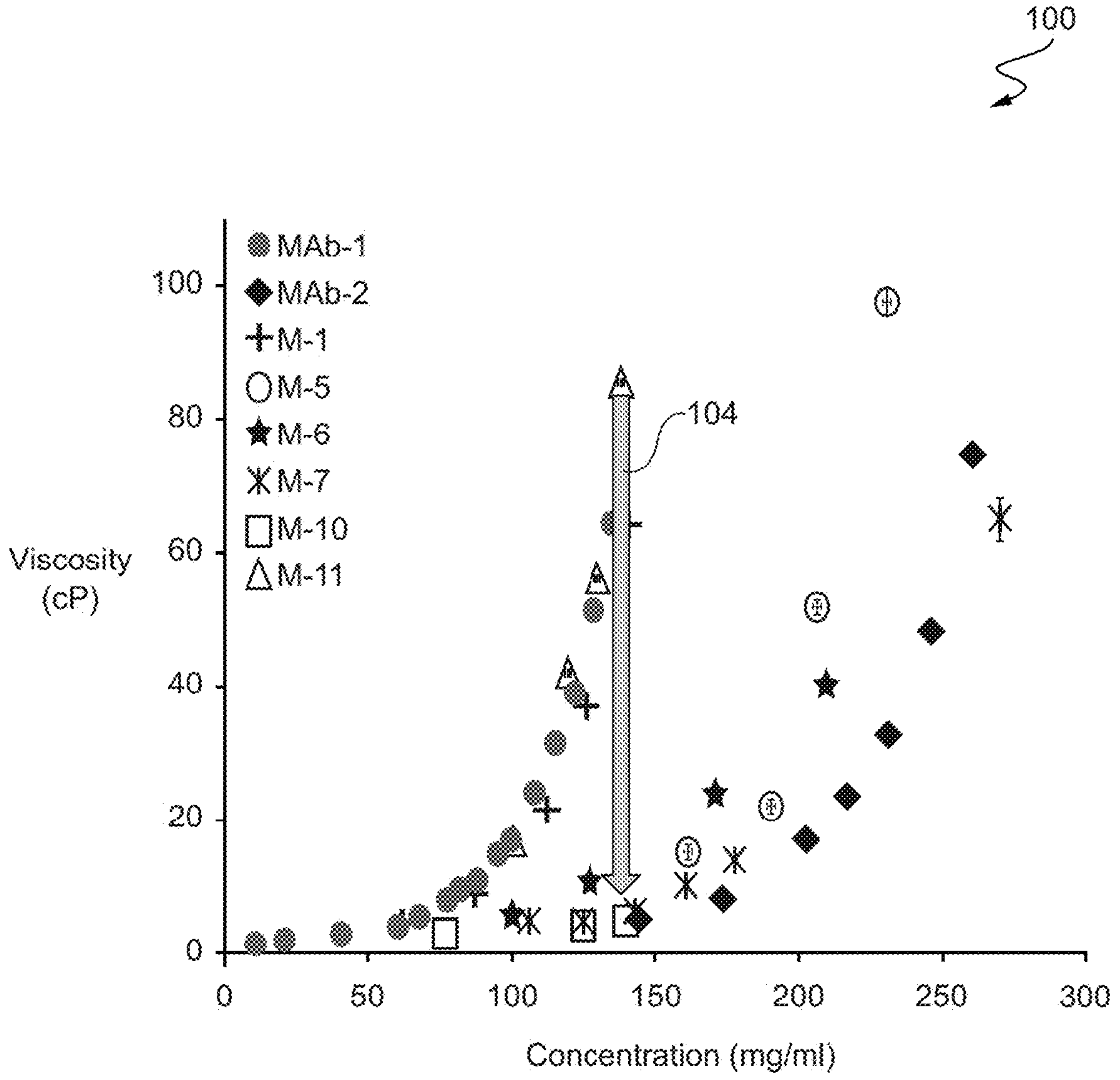
FIG. 1 depicts a chart of sample viscosities of embodiments of antibodies as a function of concentration.

FIG. 1 depicts a chart 100 that illustrates viscosity as a function of concentration of a first mAb (Mab-1), a second mAb (Mab-2), a first mutation (M-1), a second mutation (M-5), a third mutation (M-6), a fourth mutation (M-7) a fifth mutation (M-10), and a sixth mutation (M-11). The concentration of the mAbs and the mutations in a solution, in units of milligrams per milliliter (mg/ml), is measured on a horizontal axis. Viscosity, in units of centipoise (cP), is measured on a vertical axis. As concentration increases, viscosity for a given mAb or mutation also increases. Viscosity can vary greatly between different mAbs or mutations. For reference, water has a viscosity of about 1 cP, milk has a viscosity of about 3 cP, motor oil has a viscosity of about 85 to 145 cP, and the mAbs and mutations have a viscosity that ranges from about 1 cP to about 100 cP. As seen in the chart, and marked by arrow 104, the viscosity of the fifth mutation (M-10) is much less than the viscosity of the sixth mutation (M-11), for the same concentration of about 140 mg/ml. There are about 3 to 5 point mutations in the antibody variable domain between the fifth mutation (M-10) and the sixth mutation (M-11). Thus, 3 to 5 point mutations in the antibody variable domain may be used to significantly reduce viscosity in some embodiments. It would be beneficial from a cost, time, and/or human labor perspective to determine early and in silico which mAbs and/or mutations among similarly functioning mAbs would be prohibitively viscous before developing a composition. For example, the fifth mutation (M-10) is a better candidate to develop than the sixth mutation (M-11).

I.B. Coarse-Grain Modeling

Modeling of molecules can be used to estimate the viscosity of the molecules in a solution. A composition's viscosity can depend on many different types of variables relating to the physical and chemical characteristics of the molecule. For example, a composition's viscosity can depend on a degree to which molecules in the composition self-assemble. Increased self-association can lead to increased viscosity.

Figure 2A:
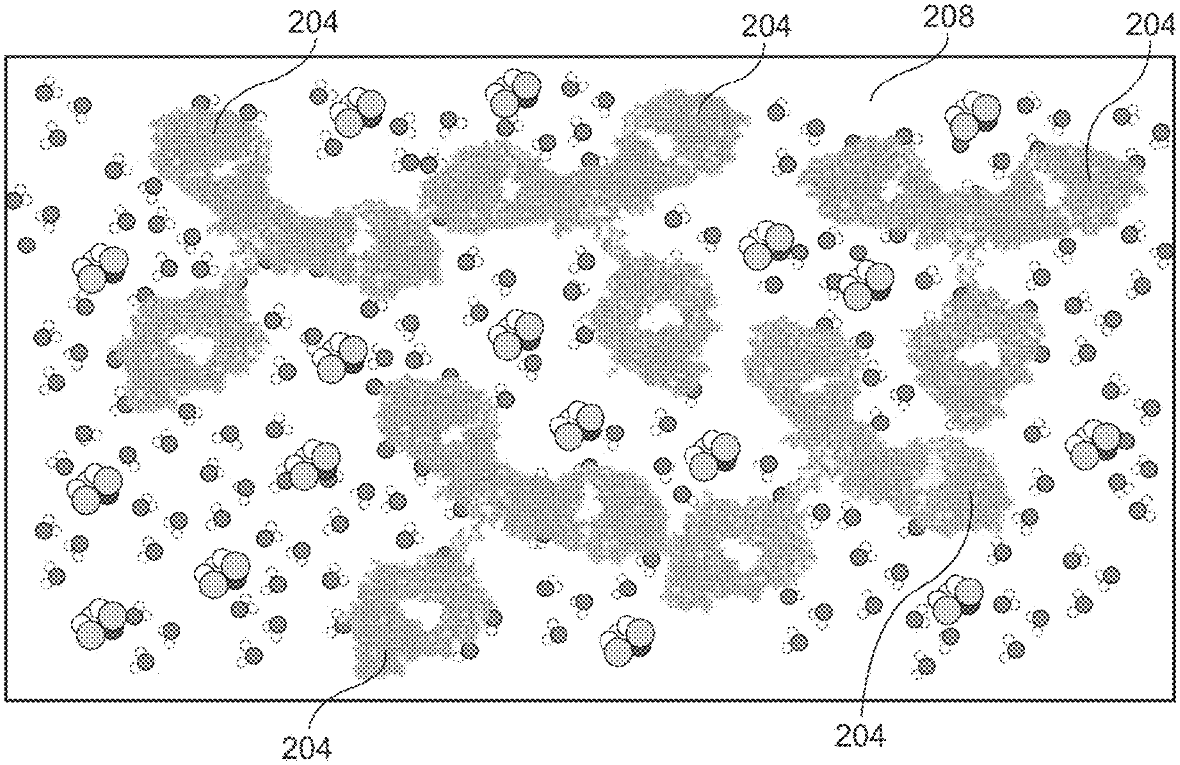
FIG. 2A illustrates an schematic example of a full-atom simulation of antibodies.

One approach for modeling viscosity of a composition can include performing "full" atom-scale modeling of the physical properties of a molecule of the composition. FIG. 2A illustrates an schematic example of a full-atom viscosity simulation. In FIG. 2A, several "full" atom models 204 of molecules are simulated in a solution 208. In the full atom model 204, each atom of a molecule is tracked, and an electric field of the molecule is calculated using electric potentials of each atom. Electric fields of the full atom models 204 interact with each other in the solution 208.

Though the full-atom viscosity simulation can be very accurate for small molecule compounds generally assembled through traditional chemistry techniques, this approach can be computationally intense for molecules of the size of antibodies because computation resources used for simulating molecular interactions scales with the number of atoms in a molecule. Small molecules can have less than one-hundred atoms, whereas polymers, such as antibodies, can have hundreds or thousands of atoms. A molecule is a group of atoms bonded together. The term "polymer," as used herein, is used to refer to a molecule that includes multiple similar units that are connected via bonds. A polymer can include a polypeptide that includes multiple amino acids. A polymer can be or can include a protein, an antibody, an oligosaccharide, DNA and/or RNA. Amino acids within the polymer can be linked together via peptide bonds. The polymer can include a protein including any protein modality, such as an amino acid substituted (unnatural amino acid), alternate glycation, protein, DNA complex and/or virus surface-coat protein. The polymer may be linear or branched, it may comprise modified amino acids, and it may be interrupted by non-amino acids. The polymer may include a backbone that includes a first set of amino acids and one or more side chains (each including a second set of amino acids). The term also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Further, a polypeptide can include an antibody and/or antibiotic polypeptide, such as antibodies referenced below in relation to FIGS. 4A-4B.

Further, other known approaches that overly simplify modeling a molecule can be plagued by low accuracy in their estimations of viscosity. One overly simplistic approach is to develop a "lumped" model where nearby charges are lumped into one value. Examples of a "lumped" model include:

Chaudhri, A., I. E. Zarraga, T. J. Kamerzell, J. P. Brandt, T. W. Patapoff, S. J. Shire, and G. A. Voth, 2012. Coarse-Grained Modeling of the Self-Association of Therapeutic Monoclonal Antibodies. *The Journal of Physical Chemistry B* 116:8045-8057.

Chaudhri, A., I. E. Zarraga, S. Yadav, T. W. Patapoff, S. J. Shire, and G. A. Voth, 2013. The Role of Amino Acid Sequence in the Self-Association of Thera-peutic Monoclonal Antibodies: Insights from Coarse-Grained Modeling. *The Journal of Physical Chemistry B* 117:1269-1279.

Buck, P. M., A. Chaudhri, S. Kumar, and S. K. Singh, 2015. Highly Viscous Antibody Solutions Are a Consequence of Network Formation Caused by Domain-Domain Electrostatic Complementarities: Insights from Coarse-Grained Simulations. *Molecular Pharmaceutics* 12:127-139.

Wang, G., Z. Varga, J. Hofmann, I. E. Zarraga, and J. W. Swan, 2018. Structure and Relaxation in Solutions of Monoclonal Antibodies. *The Journal of Physical Chemistry B* 122:2867-2880.

Figure 2B:
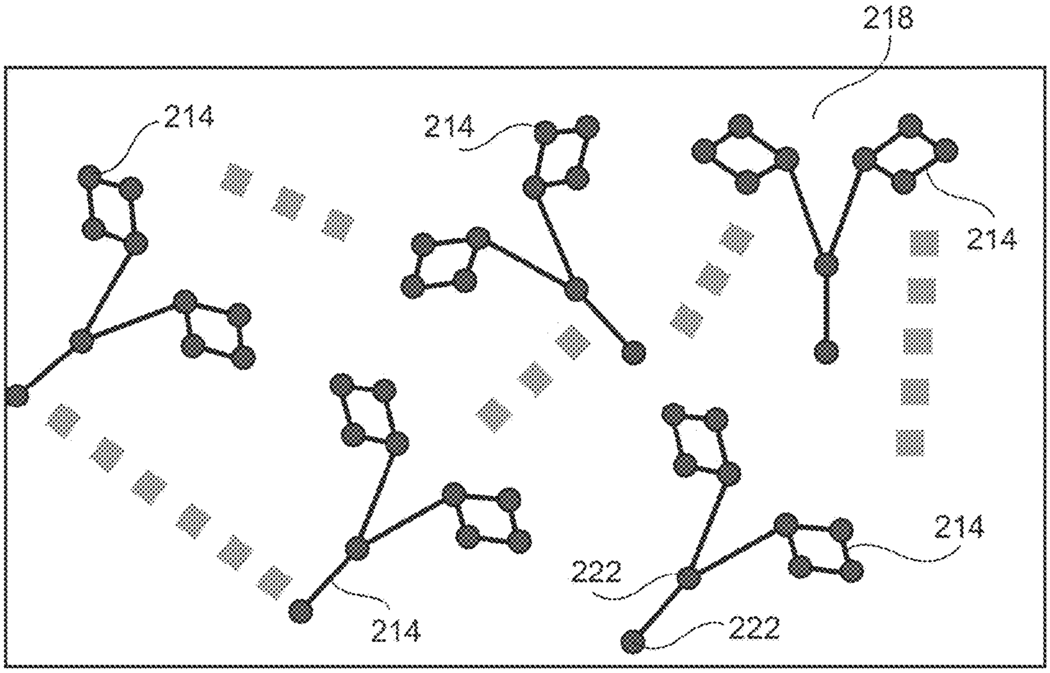
FIG. 2B illustrates an schematic example of a coarse-grain simulation of antibodies.

FIG. 2B illustrates an example of a coarse-grained viscosity simulation. A coarse-grained (CG) model 214 is created and duplicated many times to simulate several CG models 214 in a solution 218. Each site 222 (sometimes referred to as a bead or a node) of the CG model 214 is tracked, and electric fields of the CG models 214 are calculated interacting with each other using a charge at each site 222 of the CG models 214. Since there are many more atoms in the full atom models 204 than sites 222 in the CG models 214, simulating CG models 214 in solution is much quicker (e.g., less computationally intense) than simulating full atom models 204 in solution. Further, a CG model 214 can be created for different variants of a molecule (e.g., by changing a charge value at one or more sites 222 of a CG model 214), and variants of the molecule can be simulated much more quickly than creating full atom model 204 variants. The simulation using CG models 214 can predict one or more properties of a molecule, such as viscosity. By simulating properties of variants of molecules, a particular variant can be selected based on a desired property, such as lower viscosity.

In FIG. 2B, the number of sites 222 of each CG model 214 is ten. In addition to the number of sites 222, the design of a CG model 214 can also include the locations of sites 222 and the relationships between sites 222 to create a CG model 214 of a molecule. For example, a number of sites 222 with unique charge values can be selected to equal a number of molecular multipole moments used to approximate an electric field of a molecule. The term "multipole moments," as used herein, refers to a series expansion of an electrical potential of a molecule. The series expansion is traditionally in a spherical coordinate system using Legendre polynomials, though other coordinate systems or polynomials could be used. Locations of sites 222 can be chosen to have more sites in the Fab region(s) than the Fc region. Relationships between sites can be chosen to reduce computation by having sites 222 on one arm mirror sites on another arm. For example, by fixing geometry of sites 222, and modeling one arm identical to another arm (e.g., left arm identical to the right arm), there can be four degenerate positions and/or charges of sites 222 (e.g., as described in conjunction with FIG. 3 below).

FIG. 2A assumes an example simulation where there are five full atom models 204. By contrast, FIG. 2B assumes an example where there are five CG models 214, which correspond to the five full atom models 204 in FIG. 2A. Due to the number of molecules that make up most antibodies, each full atom model 204 can include as many as 10,000 or more charges, whereas each CG model 214 generally has less than 100, 50, 25, 20, 15, 10, 8, or fewer charges. Having less charges to track for each CG model 214 makes the coarse-grained viscosity simulation significantly less computationally intense than the full-atom viscosity simulation in FIG. 2A. Accordingly, coarse-grained modeling can enable a physics-based simulation of antibody self-association without performing full (e.g., atom-level) calculations.

Stated another way, a number of sites 222, location of sites 222, and/or relationships between sites 222 can be strategically selected to generate a CG model 214 that accurately simulates an electric field of a molecule and is less computationally intense to simulate in a solution than a full-atom model of the molecule.

II. Modeling an Antibody Molecule

The term "antibody," as used herein, is used to refer to a polypeptide structure such as monoclonal antibody (mAb) having an antigen-binding site. An antibody is generally a Y-shaped protein having a first arm, a second arm, and a fragment crystallizable (Fc) region. The Fc region can be considered as a base of the Y-shaped protein. The first arm and the second arm contain antigen-binding sites and can be referred to as a fragment antigen-binding (Fab) region. In some disease settings, for example an acute treatment where long half-life is undesirable or in a tissue environment where an Fc region recycling receptor (FcRn) is not active, the Fab region may be preferred over the intact mAb. Though an antibody is used in examples because many drugs have similar features as antibodies (e.g., y-shaped), CG models can be created for molecules of other shapes.

II.A. Sample Coarse-Grain Model

Figure 3:
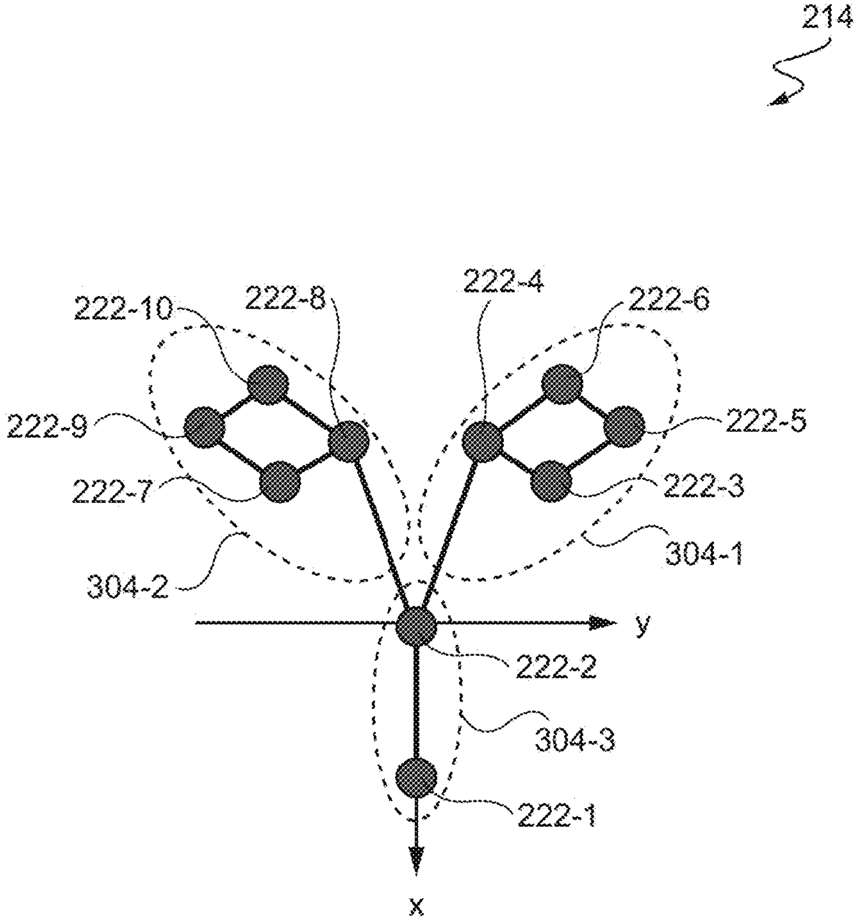
FIG. 3 illustrates an example of a coarse-grain model of an antibody.

FIG. 3 illustrates an example of a CG model 214 of an antibody molecule. The CG model 214 has a "Y" shape and is shown in relation to a chosen x-axis and a y-axis. The CG model 214 has a first arm 304-1, a second arm 304-2, and a third arm 304-3. CG model 214 also includes ten sites 222: a first site 222-1, a second site 222-2, a third site 222-3, a fourth site 222-4, a fifth site 222-5, a sixth site 222-6, a seventh site 222-7, eighth site 222-8, a ninth site 222-9, and a tenth site 222-10. The first site 222-1 and the second site 222-2 are part of the third arm 304-3. The third site 222-3, the fourth site 222-4, the fifth site 222-5, and the sixth site 222-6 are part of the first arm 304-1. The seventh site 222-7, the eighth site 222-8, the ninth site 222-9, and the tenth site 222-10 are part of the second arm 304-2. The sites 222 are on the x/y plane. Sites 222 are located in the x/y plane because the antibody molecule is assumed to be roughly symmetrical in the z-direction, e.g., the x/y plane is a plane of symmetry of the antibody molecule.

The second site 222-2 is a branching point and an origin of the x/y coordinate system is at the branching point. The first arm 304-1 and the second arm 304-2 are below the y-axis in the negative x-direction. The third arm 304-3 is oriented along the x-axis in a positive x-direction. The first arm 304-1 extends in a positive y-direction, and the second arm 304-2 extends in a negative y-direction. The first arm 304-1 and the second arm 304-2 have a symmetrical relationship about the x-axis.

The first arm 304-1 and the second arm 304-2 are configured to model the Fab region of the antibody molecule. The third arm 304-3 is configured to model the Fc region of the antibody molecule. In the embodiment shown, four sites 222 are used to model the first arm 304-1; four sites 222 are used to model the second arm 304-2; and two sites 222 are used to model the third arm 304-3. A larger number of sites are used to model the Fab region than the Fc region because the sequence of antibodies are primarily different in the Fab region where the antigen binding site is located. This variability is also the main reason different antibodies have different electric fields and thus viscosity in solution. By contrast, the Fc region is often very similar in different antibodies, and thus does not significantly play into the differences in electric field between antibodies. Accordingly, the first arm 304-1, and/or the second arm 304-2, have more sites 222 than the third arm 304-3.

II.B. Use of Multipole Moments to Approximate an Electric Field

As introduced above, the electric field of a molecule can be approximated by selecting charge values and positions for a discrete set of sites 222 so that a combined electric field of the discrete set of sites 222 approximates a plurality of low-order multipole moments of an electric field of a molecule. In some instances, low-order multipole moments are equal to or less than hexadecapole or octupole moments of the electric field.

Figure 4A:
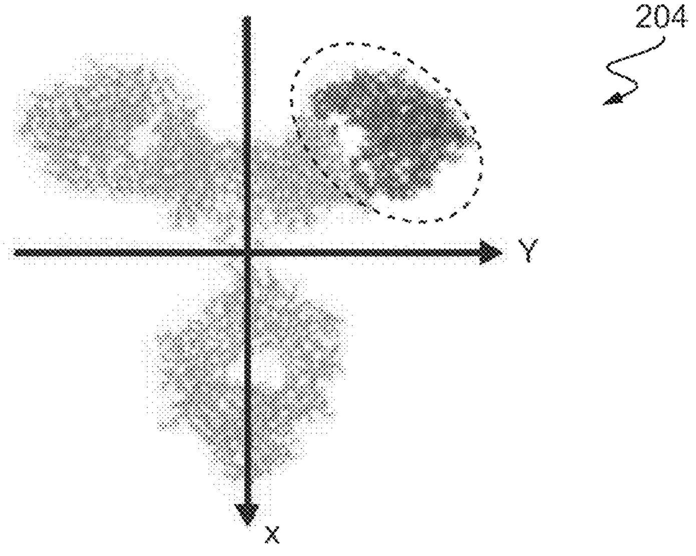
FIGS. 4A-4C show modeling an antibody, according to certain embodiments.

FIG. 4A depicts an embodiment of a full atom model 204. The full atom model 204 includes spatial relationships and charge values for atoms making up a molecule. The full atom model 204 can include 10,000 or more atoms. As mentioned previously, simulating a plurality of full atom models 204 with this many atoms interacting with each other in a solution can be computationally intense. By selecting a reduced representation using discrete set of sites 222 which have a combined electric field that approximates a plurality of multipole moments of an electric field of the full atom model 204, computations for simulating molecules interacting in a solution can be simplified.

Figure 4B:
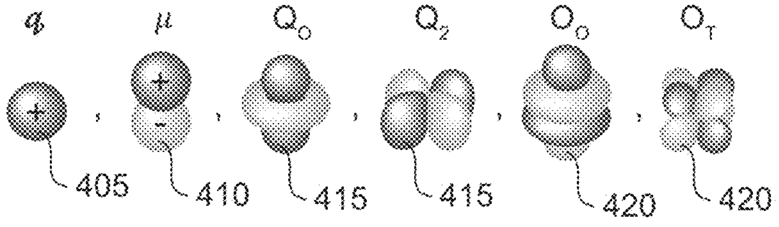

FIG. 4B depicts a number of example low-order multipole moments used to approximate the electric field of the full atom model 204. In the embodiment shown in FIGS. 3 and 4C, six multipole moments are used to approximate the electrical field of the antibody: a monopole 405, a dipole 410, two quadrupoles 415, and two octupoles 420. Experiments performed in conjunction with the example shown in FIGS. 6 and 7 have indicated using six multipoles is a good balance between accuracy and computational complexity. Further, moments higher than the dipole moment are used because the results provide higher accuracy in modeling the electric field of the antibody than simply using the monopole moment, dipole moment, or lumped model. In other embodiments, additional or fewer multipole moments could be used.

Figure 4C:
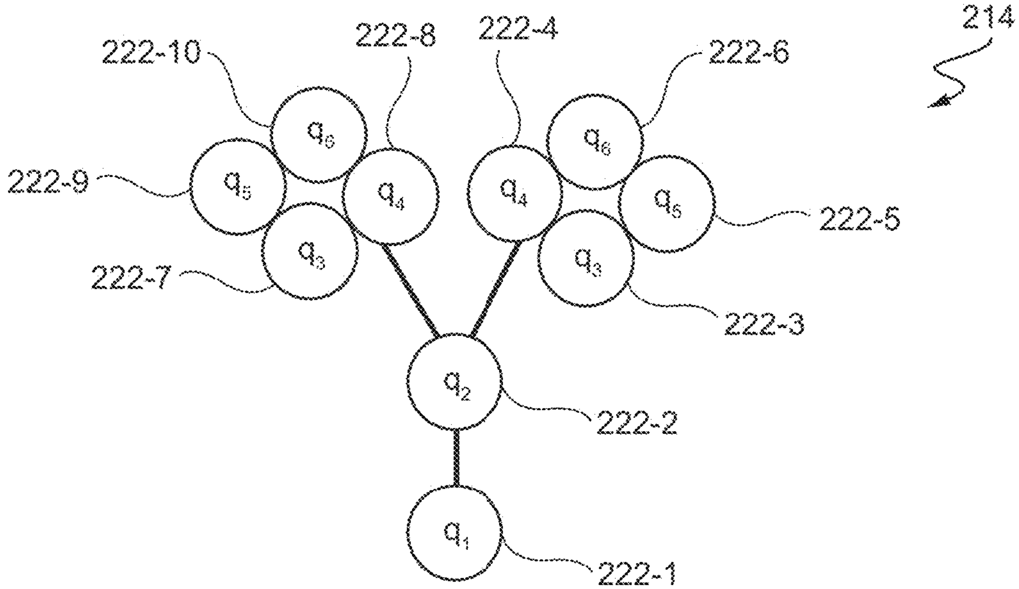

FIG. 4C depicts an embodiment of charge values at sites 222 of a CG model 214. The first site 222-1 has a first charge value $q_1$, the second site 222-2 has a second charge value $q_2$, the third sites 222-3 has a third charge value $q_3$, the fourth site 222-4 has a fourth charge value $q_4$, the fifth site 222-5 has a fifth charge value $q_5$, and the sixth site 222-6 has a sixth charge value $q_6$. Charges of sites 222 of the second arm mirror charge values q of sites 222 of the first arm. Accordingly, the seventh site 222-7 mirrors the third site 222-3 and has a charge value equal to the third charge value $q_3$; the eighth site 222-8 mirrors the fourth site 222-4 and has a charge value equal to the fourth charge value $q_4$; the ninth site 222-9 mirrors the fifth site 222-5 and has a charge value equal to the fifth charge value $q_5$; the tenth site 222-10 mirrors the sixth site 222-6 and has a charge value equal to the sixth charge value $q_6$.

Though the example in FIG. 4C shows a CG model 214 that has symmetric arms, other embodiments do not have symmetric arms or symmetric charges in arms. Locations of sites 222 in one arm can be positioned to not mirror a location of a site 222 in the other arm. In another example, a CG model 214 contains 16 sites 222.

II. C. Calculating Charge Values for a CG Model

Figure 5:
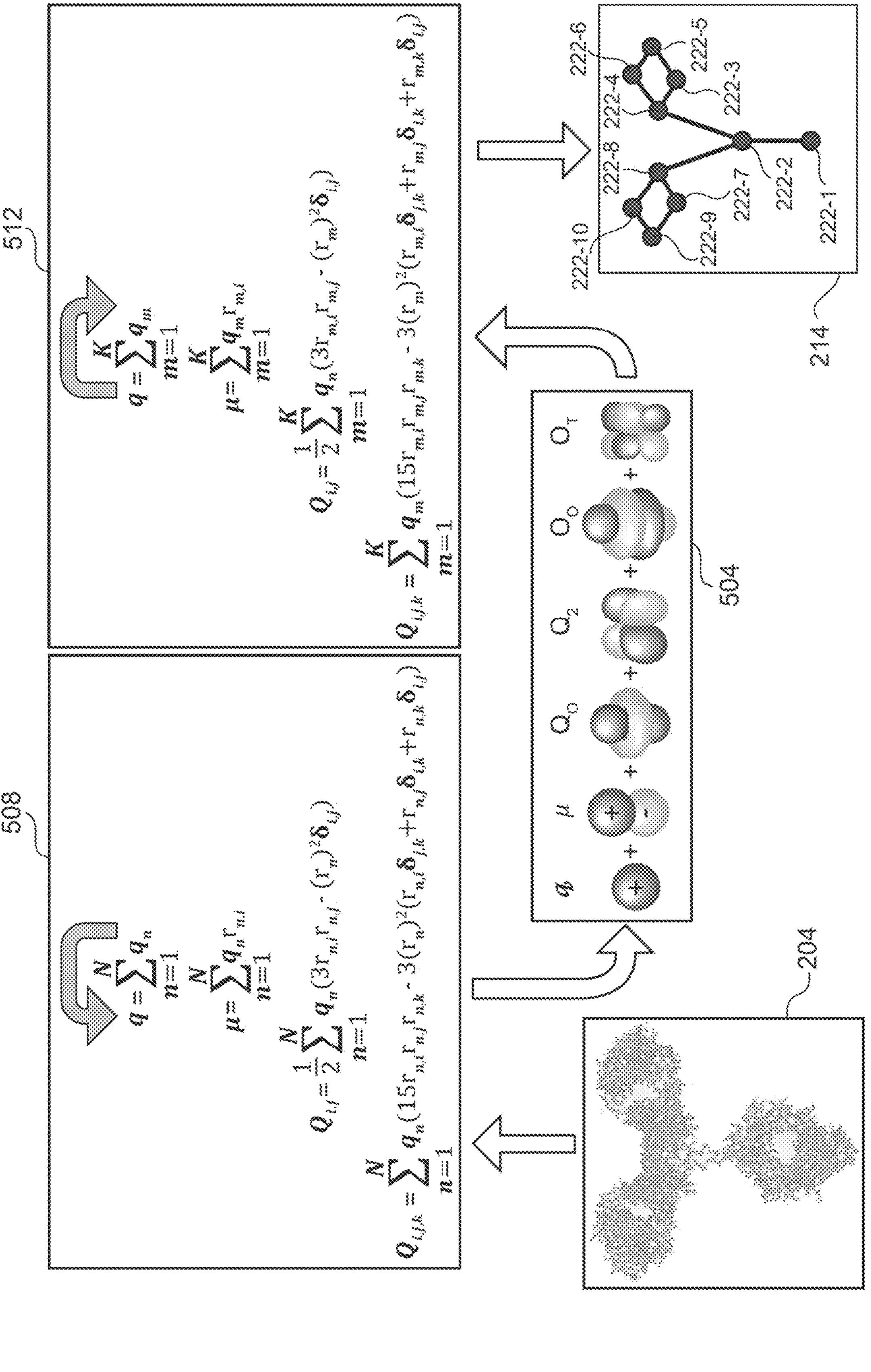
FIG. 5 shows a relationship between a coarse-grain model of an antibody and an atom model of the antibody, according to certain embodiments.

FIG. 5 shows a relationship between a CG model 214 and an underlying full atom model 204 being modeled by CG model 214, according to the example antibody embodiment discussed herein. To obtain the CG model 214 from the full atom model 204, lower-order multipole moments 504 are calculated from charges of the full atom model 204. Multipole moments can be calculated from a charge distribution as described in: Anandakrishnan R, Baker C, Izadi S, Onufriev AV (2013). Point Charges Optimally Placed to Represent the Multipole Expansion of Charge Distributions. *PLOS ONE* 8(7): e67715, the entire contents of which are incorporated herein by reference for all purposes. Box 508 contains sample equations for calculating multipole moments 504 from charges $q_n$ and spacing of atoms in the full atom model 204. In equations in box 508, N is a number of atoms in the full atom model 204. N can equal 200, 500, 1,000, 5,000, 10,000, 20,000 or more atoms. After multipole moments 504 of the electric field of the full atom model 204 are calculated, charges $q_m$ of sites 222 of the CG model 214 are calculated from the multipole moments 504. Box 512 contains equations for calculating charges $q_m$ from values of multipole moments. In equations in box 512, K is a number of unique charges $q_m$ (not necessarily the number of sites 222) in the CG model 214.

Box 512 contains equations for calculating charge values q of sites 222 using calculated electric fields of multipole moments 504 from box 508. As introduced above, the CG model 214 is designed by choosing the locations, relationships between, and number of sites 222. In this embodiment, a number of unique charges K is selected to equal a number of the multipole moments 504. In the example shown in FIGS. 4B, 4C, and 5, there are six multipole moments 504 (e.g., FIG. 4B) and K=6 (e.g., see FIG. 4C showing six charges, $q_1$ through $q_6$; and 12 sites 222, sites 222-1 through 222-12). Having as many unique charges K in the CG model 214 as there are multipole moments 504 results in an equal number of equations and unknowns, where the unknowns are the charges $q_m$ of the CG model 214. Selecting sites 222 to be in the x/y plane can further help simplify equations in box 512. Accordingly, equations in box 512 can be simplified as follows:

$$\sum_{m=1}^{6} q_m = q$$

$$\sum_{m=1}^{6} q_m x_m = \mu$$

-continued $$\sum_{n=1}^{6} q_m\left(\frac{y_m^2}{2} - x_m^2\right) = Q_0$$

$$\sum_{m=1}^{6} q_m\left(\frac{3y_m^2}{4}\right) = Q_2$$

$$\sum_{m=1}^{6} q_m\left(\frac{3y_m^2}{2} x_m - x_m^3\right) = O_0$$

$$\sum_{m=1}^{6} q_m\left(\frac{5y_m^2}{4} x_m\right) = O_T$$

The equations above are used to solve for charge values $q_m$ of sites 222 of the CG model 214 and can be solved analytically. The plurality of sites 222 of the CG model can be divided into a first subset and a second subset, where sites in the first subset have unique charge values, and sites 222 in the second subset each have a charge value equal to a charge of a site in the first subset. For example, the first subset includes the first site 222-1, the second site 222-2, the third site 222-3 the fourth site 222-4, the fifth site 222-5, and the sixth site 222-6. The second subset includes the seventh site 222-7, the eighth site 222-8, the ninth site 222-9, and the tenth site 222-10. Each site 222 in the second subset has a charge equal to a site in the first subset (e.g., see FIG. 4C). The number of sites 222 within the first subset of sites 222 is equal to the number of molecular multipole moments 504 (e.g., six). For each site 222 of the second subset, a location of the site 222 within the CG model 214 mirrors a location of a corresponding site of the first subset. For example, with respect to the x-axis, the seventh site 222-7 mirrors a location of the third site 222-3, the eighth site 222-8 mirrors a location of the fourth site 222-4, the ninth site 222-9 mirrors a location of the fifth site 222-5, and the tenth site 222-10 mirrors a location of the sixth site 222-6.

The reduced representation of charge distribution explained above, e.g., using 10 charges to represent the electrostatic field of a full-atom charge distribution, is expected to have utility in many types of computational predictive models that rely on "simplified" representations of structural properties—structural descriptors—to define the activity and properties, such as quantitative structure-activity relationship (QSAR) models as well as machine-learning-based methods. For example, the charge values on the 10-bead CG model of an antibody can be fed into a machine-learning algorithm, along with other biophysical properties/descriptors such as hydrophobic patches, to build a model to predict a number of physical instabilities of antibodies that depend on antibody overall charge distribution, namely aggregation, antibody elution behavior, clearance, gelation, and viscosity.

Representing complex charge distributions—full-atom—by a small number of point charges (e.g., 10 charges) can be particularly utilized in coarse-grained modeling that relies on a reduced (in comparison with full-atom) representation of complex systems to simulate the behavior of the system. Coarse-grained (CG) simulations are computationally significantly more efficient than full-atom simulations because of the reduced degrees of freedom.

To run a CG simulation, multiple copies of the CG model of antibodies can be arranged in a cubic lattice within a simulation box. The CG models in the simulation can interact through intermolecular interactions that can be described in terms of electrostatic and van Der Waals forces. The small number of point charges obtained above can be used to solve a Coulomb potential equation to calculate the electrostatic interactions between the CG models. A Lennard-Jones 12-6 potential energy function can be defined to describe short-range van Der Waals interactions. Additional parameters can be introduced to the CG sites, such as sigma and epsilon parameters of the LJ potential. These additional parameters can be adjusted to approximately represent the hydrophobic interactions, dispersion interactions, and/or excluded volume effects in the simulation. Solving the electrostatic and LJ interaction potentials between all the CG models in the CG simulation can provide the force on each CG site (or CG model) in the simulation box. Subsequently, the Langevin equation can be integrated in time for each CG model to analyze the physical movements of the CG models that carry a total mass equal to the total mass of the full-atom antibodies. Periodic boundary conditions can be applied in all three directions in the simulation box. The time-integration of Langevin equation of motion and the calculation of interaction forces at each intermediate time step can provide a time-dependent trajectory of the CG models in the simulation. The transitional self-diffusion coefficients of CG models can be calculated from this trajectory, and based on Stokes-Einstein relationship, this diffusion coefficient can inversely correlate with the viscosity of the antibody solution.

III. Electrical-Field Comparison

The electric field of the CG model 214 was compared to electric fields calculated from an all-atom model (e.g., full atom model 204) and a lumped coarse-grained model. The CG model 214 showed closer electric-field calculations to the all-atom model than the lumped model.

Figure 6:
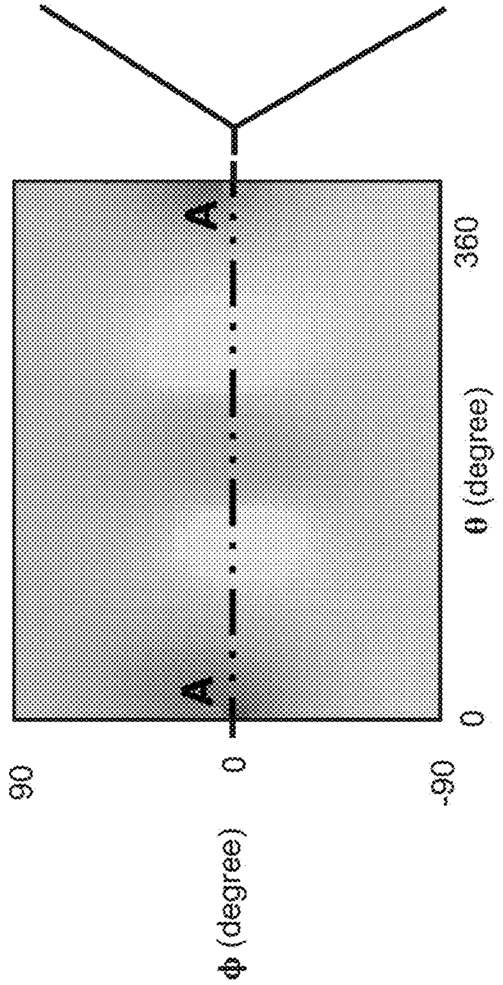
FIG. 6 shows an embodiment of an electrical field of an antibody.

FIG. 6 is a chart of the electrostatic potential of an example mAb as a function of θ and φ at a fixed distance from an origin, where θ is a rotation about the z-axis and φ is a rotation about the x-axis. FIG. 6 shows heterogeneity of electrostatic potential in a sphere around an antibody.

Figure 7:
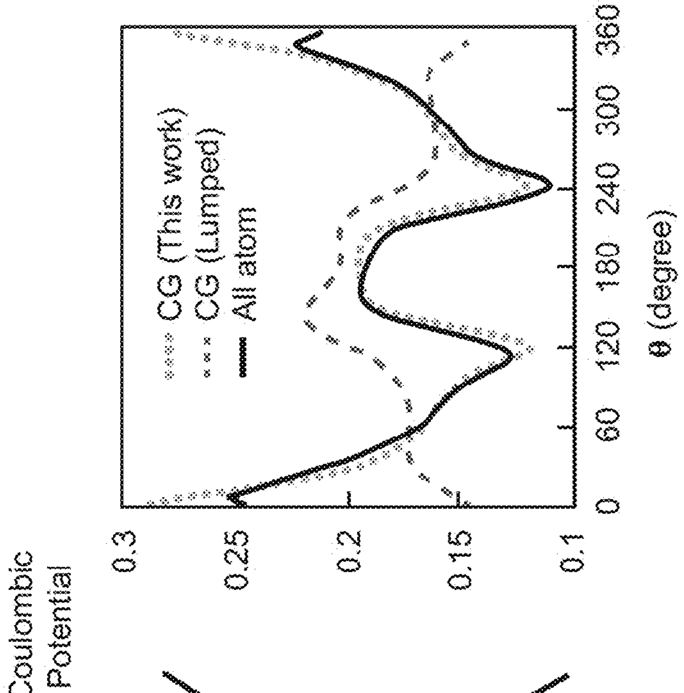
FIG. 7 depicts an example comparison of electric-field calculations of different models.

FIG. 7 charts Coulombic potential for a slice of the electrostatic surface potential in FIG. 6. In FIG. 7, the potential of the all-atom model is shown as a solid line, the potential of the CG model 214 is shown as a dotted line, and the potential of the lumped model ("CG (Lumped)") is shown as a dashed line. The lumped model sums charges in the vicinity of a CG bead, and uses the sum as the charge value for the bead.

The CG sites and the force field described above were used to perform CG Langevin dynamics simulations using a Large-scale Atomic/Molecular Massively Parallel Simulator (LAMMPS) package. Initially, 91 to 1460 mAb molecules were arranged in a cubic lattice with the box size of 1300 angstroms using PACKMOL, representative of 10 to 160 mg/ml protein concentrations. Periodic boundary conditions were applied in three directions. The CG simulations were performed under constant number, volume, and temperature (NVT) conditions with use of a Langevin thermostat with the temperature set to 300 K. The CG simulations for rigid antibodies were run for 5 microseconds, using a time step of 1 ps.

As seen in FIG. 7, the CG model 214 better approximates the electric field of the all-atom model than the lumped model does. The lumped model does not consider the electric field as a whole, at a molecular level. Instead, the lumped model calculates charges at a local level. In contrast, the multipole method calculates charges for sites based on a whole molecule by considering several (e.g., more than two)

multipole moments. Accordingly, the multipole method more accurately models an electric field of a molecule.

Another approximation for an electric field of a molecule is to use a monopole moment and/or a dipole moment of a molecule. Calculations for the monopole and dipole moments are relatively simple. However, a model using just the monopole and dipole moments lack enough detail about the electric field of the molecule to provide accurate models of the molecule. Thus simulations using three, four, five, six, or more multipole moments are used to model a molecule to more accurately describe the molecule.

IV. Process for Predicting Viscosity of a Molecule

Figure 8:
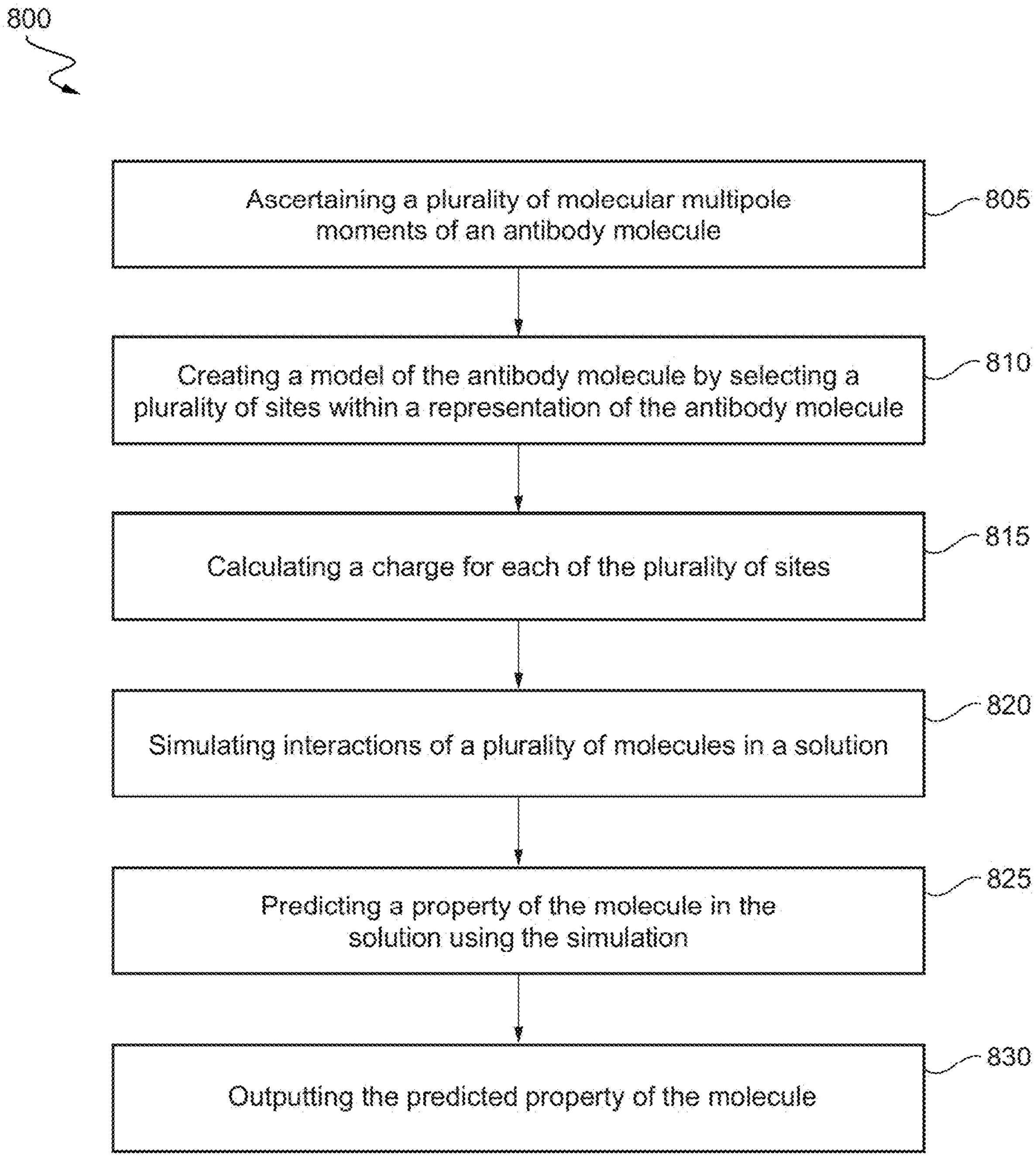
FIG. 8 illustrates a process for using a coarse-grain model to predict viscosity of an antibody.

FIG. 8 illustrates an embodiment of a process 800 for modeling viscosity of a molecule using a coarse-grain model. Process 800 begins at block 805 with ascertaining a plurality of molecular multipole moments of an antibody molecule. For example, multipole moments 504 are calculated as described in conjunction with FIG. 5 by calculating multipole moments 504 from an all-atom model of the molecule. Ascertaining the plurality of molecular multipole moments can be performed by other ways than by calculating the plurality of molecular multipole moments. For example, in some instances, ascertaining the plurality of molecular multipole moments is performed by receiving data about the plurality of molecular multipole moments (e.g., receiving a data file comprising with information of the plurality of molecular multipole moments, such as lower-order multipole moment calculations for an electric field of the antibody molecule).

In block 810, a model of the antibody molecule is created by selecting a plurality of sites within a representation of the antibody molecule. For example, sites 222 of the CG model 214 in FIGS. 3-5 are selected. In some instances, selecting sites includes determining locations of, and/or relative distances between, sites. In some embodiments, the same structure (e.g., site positions, which include locations and relative distances between sites; but different charge values) is used (e.g., selected) to model different molecules. For example, a first model uses the CG structure of 10 sites 222 as depicted in FIG. 3, and a second model uses the CG structure of 10 sites 222 as depicted in FIG. 3, but the second model has different charge values $q_m$ for sites than the first model. A number sites is less than a number of atoms in the antibody molecule (e.g., to reduce computational intensity in simulating the antibody molecule in a solution).

The plurality of sites includes a first subset of sites and a second subset of sites. The first subset of sites can be chosen so that a number of sites within the first subset is equal to a number of the molecular multipole moments ascertained in block 805. The number of sites within the first subset can be chosen to equal the number of molecular multipole moments to simplify calculating values of charges of the plurality of sites, as described in conjunction with FIG. 5. In some implementations, the number of molecular multipole moments is equal to or greater than 3, 4, 5, or 6 and/or equal to or less than 20, 16, 12, or 10. In the example in FIGS. 4B and 4C, the number of molecular multipole moments is six, and a number of the plurality of sites is equal to 10. The number of the second subset of sites can be less than the number of the first subset of sites, wherein the number of the second subset of sites plus the number of the first subset of sites is equal to the number of the plurality of sites. For example, in FIG. 3 sites 222 in the first arm 304-1 and in the second arm 304-2 are part of the first subset of sites, and sites 222 in the second arm 304-2 are part of the second subset of sites.

In block 815, a charge for each site is calculated. For example, equations in box 512 of FIG. 5 are solved to find $q_n$, wherein $q_n$ are charge values for the first subset of sites. Locations of sites of the first subset of sites and the plurality of molecular multipole moments are used to calculate charge values for the first subset of sites. For each site of the second subset of sites, a location of the site within the representation of the antibody molecule can mirror a location of a corresponding site of the first subset of sites within the representation of the antibody molecule. For example, sites 222 of the second arm 304-2 in FIG. 3 mirror, about the x-axis, locations of sites 222 of the first arm 304-1. For each site of the second subset of sites, a charge calculated for each site is equal to a charge calculated for a corresponding site of the first subset of sites. For example, in FIG. 4C, the seventh site 222-7 has the same charge value as the third site 222-3; and the eighth site 222-8, the ninth site 222-9, and the tenth site 222-10 have the same charge values as the fourth site 222-4, the fifth site 222-5, and the sixth site 222-6 respectively. A combination of charge values for the sites approximates the plurality of molecular multipole moments of the antibody molecule.

In block 820, interactions of a plurality of molecules in a solution are simulated. At least one molecule of the plurality of molecules simulated in the solution is an instance of the model of the antibody molecule. In some instances, each molecule of the plurality of molecules simulated in the solution are an instance of the model of the antibody molecule (e.g., if there is only one molecule to be used). In other instances, two or more types of molecules can be simulated in a solution by using two or more molecular coarse-grain models. The interactions are simulated based on the charges calculated for each of the plurality of sites within the representation of the antibody molecule. In block 825, a property of the solution is predicted using the simulation. For example, aggregation, antibody elution behavior, clearance, gelation, and/or viscosity are predicted by simulating the CG model in solution. A viscosity of the solution can be predicted using a concentration of one or more molecules in the solution. In some instances, a viscosity of the solution is predicted as a function of the concentration of the one or more molecules in the solution.

In block 830, the predicted property of the solution is outputted. For example, the predicted property of the solution is sent to a file, displayed on a screen, or emailed to a specified email address. In some instances, the process 800 further includes comparing the property of the solution to a predetermined threshold; moving forward with manufacturing; selecting the molecule for further processing (e.g., alongside other factors such as clearance rate); and/or facilitating development of a liquid solution comprising the one or more molecules as at least part of a therapeutic agent. For example, the development of a liquid solution comprising the one or more molecules as at least part of a therapeutic agent may be facilitated based, at least partially, on the predicted property being below or above the predetermined threshold. In some instances, the process 800 further includes, based on the predicted property of the solution: (i) adding the antibody molecule to a list of potential polypeptides to be used as at least part of a therapeutic agent, (ii) removing the antibody molecule from the list of potential polypeptides to be used as at least part of the therapeutic agent, (iii) ranking the antibody molecule within the list of potential polypeptides to be used as at least part of the therapeutic agent, or (iv) a combination thereof.

By simulating interactions of the plurality of molecules in the solution, a viscosity of the plurality of molecules in the solution can be predicted accurately, without using a computationally-intense, all-atom model. Thus using a coarse-grain model of a molecule can improve the functioning of a computer by reducing calculations for determining viscosity a liquid solution and/or speeding up processing of the computer for simulating viscosity of molecules. By predicting the viscosity of molecules early, molecules can be rejected before spending significant developmental time and/or expense to only find out that the molecule in solution has too high of viscosity to be effectively used.

V. Sixteen-Site CG Model

Figure 9:
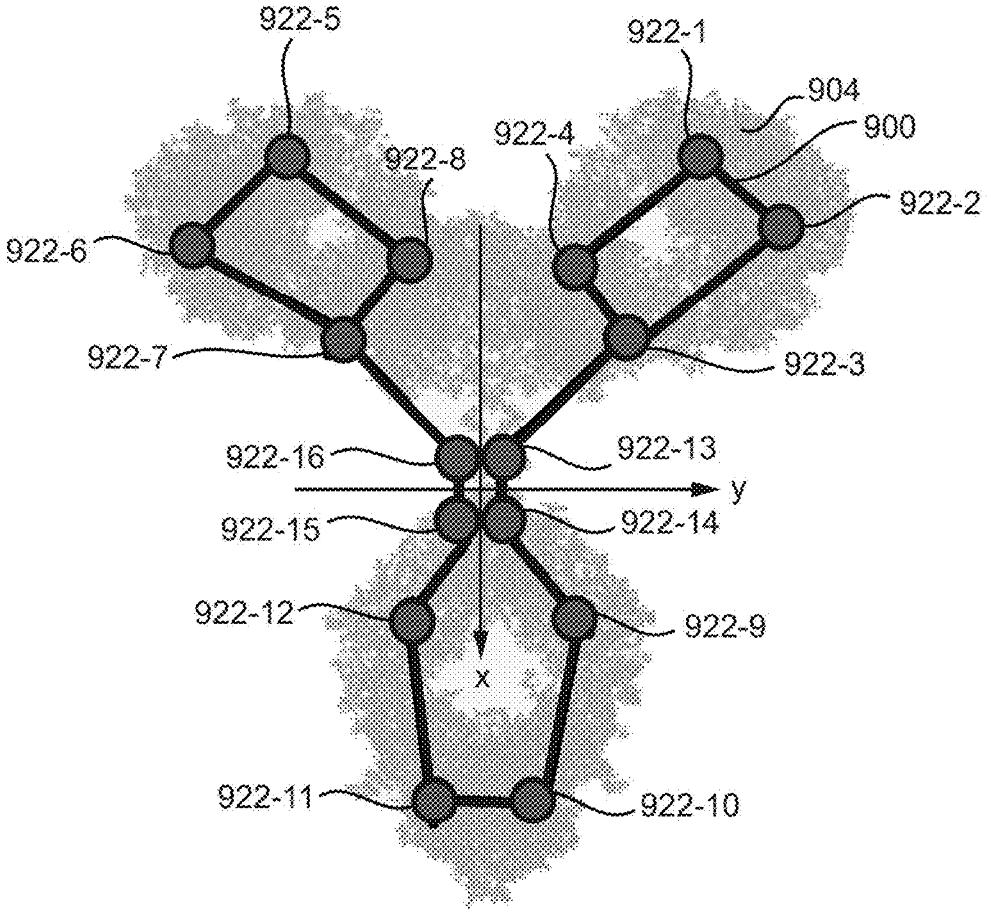
FIG. 9 illustrates another example of a coarse-grain model of an antibody.

In another example of a CG model, sixteen sites are used to model a molecule. FIG. 9 depicts a CG model 900 superimposed over a full-atom model 904. The CG model 900 comprises sixteen sites 922. There are four sites 922 in a first arm (sites 922-1, 922-2, 922-3, and 922-4); four sites 922 in a left arm (sites 922-5, 922-6, 922-7, and 922-8); four sites in a third arm (sites 922-9, 922-10, 922-11, and 922-12); and four sites in a hinge region (922-13, 922-14, 922-15, and 922-16).

Each site 922 has an independent charge value. Sixteen multipole moments are used to determine charge values for the sixteen sites 922. Multipole moments from the monopole through the octupole are used for the sixteen multipole moment. A number of independent tensor elements are sixteen: monopole (1); dipole (3); quadrupole (5), and octupole (7). Tensor elements of multipole moments can be found in: Kielich S. and Zawodny R., Tensor elements of the molecular electric multipole moments for all point group symmetries, *Chemical Physics Letters*, Volume 12, Issue 1, 1971, Pages 20-24, ISSN 0009-2614, the entire contents of which are incorporated herein by reference for all purposes.

By having sixteen unique tensor elements and sixteen charges at sites 922, charge values for sites 922 can be calculated numerically. Since there are sixteen unique charges for sites 922, and only sixteen sites 922, sites 922 are not necessarily mirrored about the x axis (though they could be). By having sixteen unique sites, many different geometries of molecules can be modeled.

VI. Additional Considerations

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implemented method comprising:

ascertaining a plurality of molecular multipole moments of an antibody molecule;

creating a model of the antibody molecule by selecting a plurality of sites within a representation of the antibody molecule, wherein:

a total number of the plurality of sites is less than a total number of atoms in the antibody molecule;

the plurality of sites comprises a first subset of the plurality of sites and a second subset of the plurality of sites; and a total number of sites within the first subset of the plurality of sites is equal to a total number of molecular multipole moments within the plurality of molecular multipole moments;

calculating a charge for each of the plurality of sites, wherein:

a combination of calculated charges for the plurality of sites approximates the plurality of molecular multipole moments of the antibody molecule; and for each site of the second subset of the plurality of sites, a charge calculated for each site is equal to a charge calculated for a corresponding site of the first subset of the plurality of sites;

executing a molecular dynamics simulation representing a plurality of molecules in a solution to generate a time-dependent trajectory data for the model of the antibody molecule, wherein at least one molecule of the plurality of molecules is an instance of the model of the antibody molecule and the molecular dynamics simulation simulates interactions based on the charges calculated for each of the plurality of sites within the representation of the antibody molecule;

predicting a property of the solution using data from the molecular dynamics simulation; and outputting the predicted property of the solution.

2. The computer-implemented method of claim 1, wherein for each site of the second subset of the plurality of sites, a location of the site within the representation of the antibody molecule mirrors a location of the corresponding site of the first subset of the plurality of sites within the representation of the antibody molecule.

3. The computer-implemented method of claim 1, wherein locations of sites of the first subset of the plurality of sites and the plurality of molecular multipole moments are used to calculate charge values for the first subset of the plurality of sites.

4. The computer-implemented method of claim 1, wherein ascertaining the plurality of molecular multipole moments of the antibody molecule is performed by: (i) modeling a charge distribution of the antibody molecule using an atomic model of the antibody molecule, or (ii) receiving an electric field calculation of the antibody molecule.

5. The computer-implemented method of claim 1, wherein:

a total number of the second subset of the plurality of sites is less than the total number of the first subset of the plurality of sites; and the total number of the second subset of the plurality of sites plus the total number of the first subset of the plurality of sites is equal to the total number of the plurality of sites.

6. The computer-implemented method of claim 1, wherein:

the antibody molecule is a Y-shaped protein having a first arm, a second arm, and a third arm;

the first arm and the second arm are part of a Fab (antigen-binding fragment) region;

the third arm is part of an Fe (fragment crystallizable) region;

the first subset of the plurality of sites includes sites on the first arm and the third arm; and the second subset of the plurality of sites includes sites on the second arm, so that the second arm is modeled as a mirror image of the first arm.

7. The computer-implemented method of claim 1, further comprising, based on the predicted property of the solution: (i) adding the antibody molecule to a list of potential polypeptides to be used as at least part of a therapeutic agent, (ii) removing the antibody molecule from the list of potential polypeptides to be used as at least part of the therapeutic agent, (iii) ranking the antibody molecule within the list of potential polypeptides to be used as at least part of the therapeutic agent, or (iv) a combination thereof.

8. A system comprising:

one or more data processors; and a non-transitory, computer-readable storage medium containing instructions which, when executed on the one or more data processors, cause the one or more data processors to perform actions including:

ascertaining a plurality of molecular multipole moments of an antibody molecule;

creating a model of the antibody molecule by selecting a plurality of sites within a representation of the antibody molecule, wherein:

a total number of the plurality of sites is less than a total number of atoms in the antibody molecule;

the plurality of sites comprises a first subset of the plurality of sites and a second subset of the plurality of sites; and a total number of sites within the first subset of the plurality of sites is equal to a total number of molecular multipole moments within the plurality of molecular multipole moments;

calculating a charge for each of the plurality of sites, wherein:

a combination of calculated charges for the plurality of sites approximates the plurality of molecular multipole moments of the antibody molecule; and for each site of the second subset of the plurality of sites, a charge calculated for each site is equal to a charge calculated for a corresponding site of the first subset of the plurality of sites;

executing a molecular dynamics simulation representing a plurality of molecules in a solution to generate a time-dependent trajectory data for the model of the antibody molecule, wherein at least one molecule of the plurality of molecules is an instance of the model of the antibody molecule and the molecular dynamics simulation simulates interactions based on the charges calculated for each of the plurality of sites within the representation of the antibody molecule;

predicting a property of the solution using data from the molecular dynamics simulation; and outputting the predicted property of the solution.

9. The system of claim 8, wherein for each site of the second subset of the plurality of sites, a location of the site within the representation of the antibody molecule mirrors a location of the corresponding site of the first subset of the plurality of sites within the representation of the antibody molecule.

10. The system of claim 8, wherein locations of sites of the first subset of the plurality of sites and the plurality of molecular multipole moments are used to calculate charge values for the first subset of the plurality of sites.

11. The system of claim 8, wherein ascertaining the plurality of molecular multipole moments of the antibody molecule is performed by: (i) modeling a charge distribution of the antibody molecule using an atomic model of the antibody molecule, or (ii) receiving an electric field calculation of the antibody molecule.

12. The system of claim 8, wherein:

a total number of the second subset of the plurality of sites is less than the total number of the first subset of the plurality of sites; and the total number of the second subset of the plurality of sites plus the total number of the first subset of the plurality of sites is equal to the total number of the plurality of sites.

13. The system of claim 8, wherein:

the antibody molecule is a Y-shaped protein having a first arm, a second arm, and a third arm;

the first arm and the second arm are part of a Fab (antigen-binding fragment) region;

the third arm is part of an Fe (fragment crystallizable) region;

the first subset of the plurality of sites includes sites on the first arm and the third arm; and the second subset of the plurality of sites includes sites on the second arm, so that the second arm is modeled as a mirror image of the first arm.

14. The system of claim 8, wherein the actions further include, based on the predicted property of the solution: (i) adding the antibody molecule to a list of potential polypeptides to be used as at least part of a therapeutic agent, (ii) removing the antibody molecule from the list of potential polypeptides to be used as at least part of the therapeutic agent, (iii) ranking the antibody molecule within the list of potential polypeptides to be used as at least part of the therapeutic agent, or (iv) a combination thereof.

15. A computer-program product tangibly embodied in a non-transitory machine-readable storage medium, including instructions configured to cause one or more data processors to perform actions including:

ascertaining a plurality of molecular multipole moments of an antibody molecule;

creating a model of the antibody molecule by selecting a plurality of sites within a representation of the antibody molecule, wherein:

a total number of the plurality of sites is less than a total number of atoms in the antibody molecule;

the plurality of sites comprises a first subset of the plurality of sites and a second subset of the plurality of sites; and a total number of sites within the first subset of the plurality of sites is equal to a total number of molecular multipole moments within the plurality of molecular multipole moments;

calculating a charge for each of the plurality of sites, wherein:

a combination of calculated charges for the plurality of sites approximates the plurality of molecular multipole moments of the antibody molecule; and for each site of the second subset of the plurality of sites, a charge calculated for each site is equal to a charge calculated for a corresponding site of the first subset of the plurality of sites;

executing a molecular dynamics simulation representing a plurality of molecules in a solution to generate a time-dependent trajectory data for the model of the antibody molecule, wherein at least one molecule of the plurality of molecules is an instance of the model of the antibody molecule and the molecular dynamics simulation simulates interactions based on the charges calculated for each of the plurality of sites within the representation of the antibody molecule;

predicting a property of the solution using data from the molecular dynamics simulation; and outputting the predicted property of the solution.

16. The computer-program product of claim 15, wherein for each site of the second subset of the plurality of sites, a location of the site within the representation of the antibody molecule mirrors a location of the corresponding site of the first subset of the plurality of sites within the representation of the antibody molecule.

17. The computer-program product of claim 15, wherein locations of sites of the first subset of the plurality of sites and the plurality of molecular multipole moments are used to calculate charge values for the first subset of the plurality of sites.

18. The computer-program product of claim 15, wherein ascertaining the plurality of molecular multipole moments of the antibody molecule is performed by: (i) modeling a charge distribution of the antibody molecule using an atomic model of the antibody molecule, or (ii) receiving an electric field calculation of the antibody molecule.

19. The computer-program product of claim 15, wherein:

a total number of the second subset of the plurality of sites is less than the total number of the first subset of the plurality of sites; and the total number of the second subset of the plurality of sites plus the total number of the first subset of the plurality of sites is equal to the total number of the plurality of sites.

20. The computer-program product of claim 15, wherein:

the antibody molecule is a Y-shaped protein having a first arm, a second arm, and a third arm;

the first arm and the second arm are part of a Fab (antigen-binding fragment) region;

the third arm is part of an Fe (fragment crystallizable) region;

the first subset of the plurality of sites includes sites on the first arm and the third arm; and the second subset of the plurality of sites includes sites on the second arm, so that the second arm is modeled as a mirror image of the first arm.

* * * * *